(12) United States Patent
Huang et al.

(10) Patent No.: US 12,668,764 B2
(45) Date of Patent: Jun. 30, 2026

(54) ORGANIC-WASTE-RECYCLING APPARATUS FOR FAST FORMATION OF COMPOST

(71) Applicant: Minima Technology Co., Ltd., Yunlin County (TW)

(72) Inventors: Chien-Ming Huang, Yunlin County (TW); Yu-Kai Huang, Yunlin County (TW)

(73) Assignee: MINIMA TECHNOLOGY CO., LTD., Yunlin County (TW)

( * ) Notice: Subject to any disclaimer, the term of this patent is extended or adjusted under 35 U.S.C. 154(b) by 612 days.

(21) Appl. No.: 18/195,390

(22) Filed: May 10, 2023

(65) Prior Publication Data

US 2024/0376414 A1     Nov. 14, 2024

(51) Int. Cl.
*C12M 1/16*     (2006.01)
*C05F 17/907*     (2020.01)

(52) U.S. Cl.
CPC ........... *C12M 21/16* (2013.01); *C05F 17/907* (2020.01)

(58) Field of Classification Search
None
See application file for complete search history.

(56) References Cited

U.S. PATENT DOCUMENTS

| | | | | |
|---|---|---|---|---|
| 10,556,840 | B1 * | 2/2020 | Bradlee | C05F 17/914 |
| 2020/0148604 | A1 * | 5/2020 | Atkinson | B02C 18/0092 |
| 2020/0353473 | A1 * | 11/2020 | Hayman | B01D 46/4227 |
| 2020/0353474 | A1 * | 11/2020 | Crepeau | B01D 46/4227 |

FOREIGN PATENT DOCUMENTS

| | | | | | |
|---|---|---|---|---|---|
| CN | 108083856 | A | * | 5/2018 | C05F 17/907 |
| CN | 110372432 | A | * | 10/2019 | C05F 17/00 |
| ES | 2382801 | T3 | * | 6/2012 | C05F 17/907 |
| KR | 101346593 | B1 | * | 1/2014 | B02C 13/30 |
| TW | M530810 | U | * | 10/2016 | |

* cited by examiner

*Primary Examiner* — William H. Beisner
*Assistant Examiner* — Julius Francis Yoh
(74) *Attorney, Agent, or Firm* — WPAT, PC

(57) ABSTRACT

An organic-waste-recycling apparatus for fast formation of compost includes a processing barrel, a grinding device, a control device, a stirring device, and a guiding device. The processing barrel has a first feeding port and a second feeding port, a mixing room, and an output. To-be-processed objects are fed into the mixing room through the first feeding port or the second feeding port. The grinding device is between the first feeding port and the mixing room. The control device adjusts the temperature and the humidity in the mixing room. The stirring device rolls and blends the to-be-processed objects in the mixing room so that the to-be-processed objects are heated evenly. The guiding device guides the water vapor generated in the mixing room back to the mixing room. The apparatus decomposes and turns organic waste into organic carbon fertilizer that has economic value in an effective and efficient way.

11 Claims, 5 Drawing Sheets

ORGANIC-WASTE-RECYCLING APPARATUS FOR FAST FORMATION OF COMPOST

BACKGROUND OF THE INVENTION

1. Technical Field

The present invention relates to recycling apparatus of organic waste, and more particularly to an organic-waste-recycling apparatus for fast formation of compost.

2. Description of Related Art

According to statistics, organic waste generated in Taiwan sums up near 500 thousand tons every year, which means that one person in Taiwan produces more than one kilogram of organic waste per day in average. It is thus envisageable that proper recycling and use of the organic waste will be supportive to preserve and protect our natural resources.

Among organic waste, kitchen waste coming from households, restaurants, and diners accounts for a large part. Experientially, when disposing kitchen waste, some people may have shells, bones, or decomposable eating utensils mixed in, and such a mixture cannot be effectively and efficiently decomposed by existing domestic composters.

As stated, since existing domestic composters are less satisfying due to their limits in terms of decomposing capacity, heating power, and grinding force, there is a pressing need for an improved approach.

SUMMARY OF THE INVENTION

The primary objective of the present invention is to provide a novel approach to recycling organic waste, particularly kitchen waste, in an effective and efficient way.

The objectives recited previously do not exclude the existence of other objectives. All objectives that can be derived by people skilled in the art by referring to the description, the claims, and/or the drawing are also considered as objectives of the present invention. Hence, objectives of the present invention are not limited to what has been described.

To achieve the foregoing objective, the present invention provides an organic-waste-recycling apparatus for fast formation of compost. In use, one or more to-be-processed objects are fed into the organic-waste-recycling apparatus for recycling. The organic-waste-recycling apparatus comprises: a processing barrel, a grinding device, a control device, a stirring device, and a guiding device. The processing barrel has a first feeding port, a second feeding port, a mixing room, and an output. The first feeding port, the second feeding port, and the output are communicated with the mixing room. The to-be-processed objects are fed into the mixing room through the first feeding port or the second feeding port. The grinding device is arranged between the first feeding port and the mixing room. The control device has a temperature-controlling unit and a humidity-controlling unit. The control device is electrically connected to the temperature-controlling unit and the humidity-controlling unit. The temperature-controlling unit is used to adjust a fermentation temperature in the mixing room. The humidity-controlling unit is used to adjust a fermentation humidity in the mixing room. The stirring device is installed in the mixing room. The stirring device has a helical cutter. The helical cutter rolls and blends the to-be-processed objects fed through the first feeding port or the second feeding port in the mixing room so that the to-be-processed objects can be evenly heated as they are rolling in the mixing room. The guiding device is installed above the processing barrel so as to guide water vapor generated in the mixing room back to the mixing room.

Thereby, the present invention provides the following features:

1. With the grinding device, the disclosed apparatus can grind large pieces of food waste or biodegradable eating utensils into scraps, thereby facilitating subsequent processing for recycling.
2. With the helical cutter rolling and blending to-be-processed objects in the mixing room, the disclosed apparatus can evenly heat the to-be-processed objects as they roll in the mixing room, so as to ensure effective and efficient fermentation and further use of the to-be-processed objects.
3. With temperature-controlling unit and the humidity-controlling unit in the control device that adjust the fermentation temperature and the fermentation humidity in the mixing room, the disclosed apparatus can ferment the to-be-processed objects effectively and efficiently while shortening the fermentation cycle of the to-be-processed objects.
4. With the guiding device that guides water vapor back to the mixing room, the disclosed apparatus can prevent water vapor from escaping from the mixing room.

BRIEF DESCRIPTION OF THE DRAWINGS

The invention as well as a preferred mode of use, further objectives and advantages thereof will be best understood by reference to the following detailed description of illustrative embodiments when read in conjunction with the accompanying drawings, wherein:

FIG. 2 is a schematic front view of the organic-waste-recycling apparatus;

DETAILED DESCRIPTION OF THE INVENTION

Figure 1:
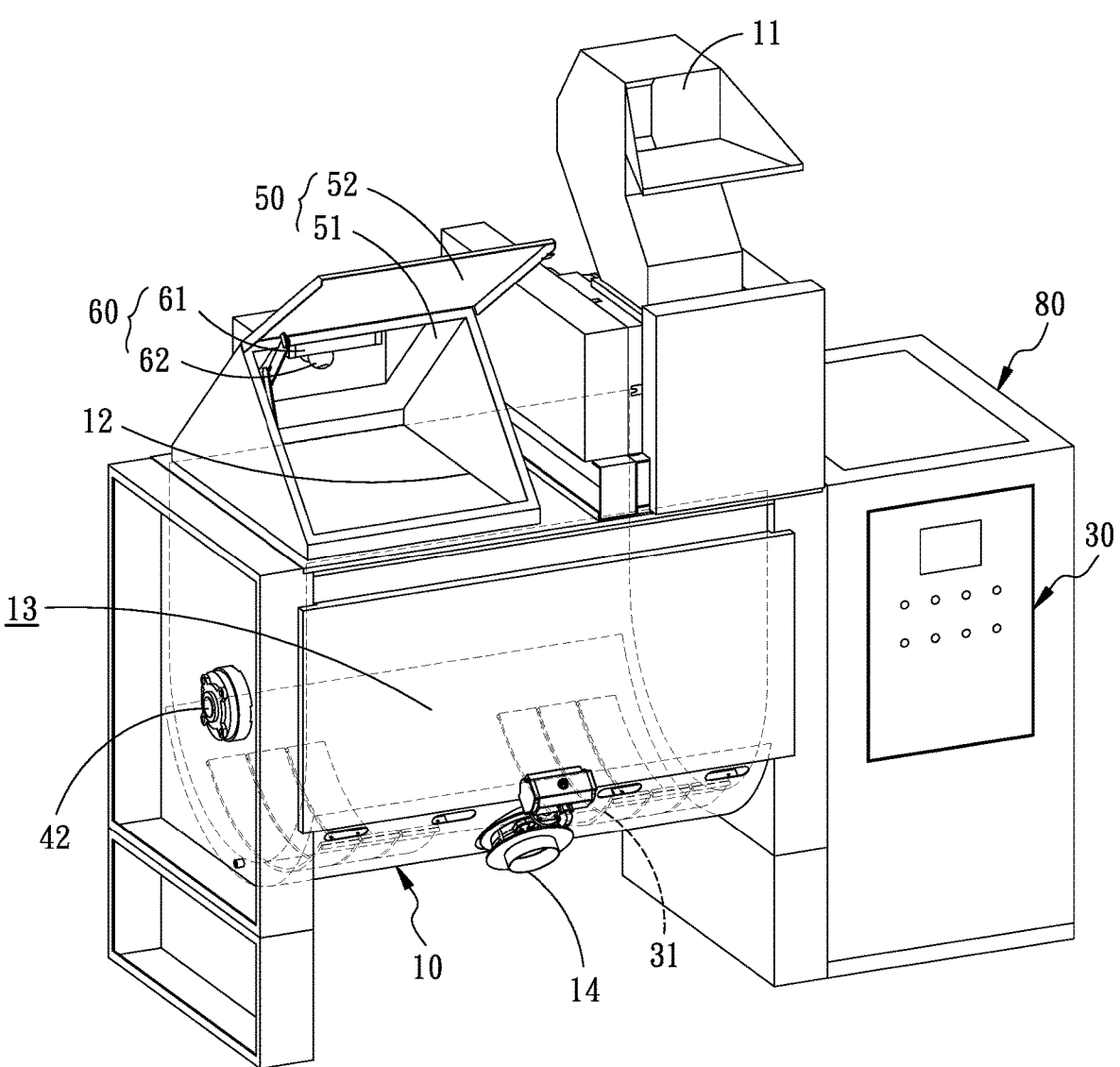
FIG. 1 is a schematic perspective view of an organic-waste-recycling apparatus according to a preferred embodiment of the present invention.

For further illustrating the means and functions by which the present invention achieves the certain objectives, the following description, in conjunction with the accompanying drawings and preferred embodiments, is set forth as below to illustrate the implement, structure, features and effects of the subject matter of the present invention. It is to be understood that the components as well as deformation and displacement thereof shown in the accompanying drawings are depicted for the sake of easy explanation and need not to be made to exact scale.

The preferred embodiments of the present invention provided herein are not intended to limit the technical principles of the present invention to any specific embodiment. Any modification, equivalent replacement, and improvement made under the spirit and principle of the present invention shall be included in the scope of the present invention.

Referring to FIG. 1 through FIG. 5, the present invention provides an organic-waste-recycling apparatus 100 for fast formation of compost. The organic-waste-recycling apparatus 100 is used to recycle one or more to-be-processed objects 1. The organic-waste-recycling apparatus 100 comprises: a processing barrel 10, a grinding device 20, a control device 30, a stirring device 40, and a guiding device 50. The to-be-processed objects 1 may be food waste such as solid or liquid leftovers from meals and bones, or may be biodegradable eating utensils, such as knives and forks, bowls, and plates. The to-be-processed objects 1 may additionally include biodegradable containers, packing materials, garden waste, and biodegradable polymer composites.

In the embodiment of the present invention, the processing barrel 10 has a first feeding port 11, a second feeding port 12, a mixing room 13, and an output 14. The first feeding port 11, the second feeding port 12, and the output 14 are communicated with the mixing room 13. The to-be-processed objects 1 are fed into the mixing room 13 through the first feeding port 11 or the second feeding port 12. Specifically, if the to-be-processed objects 1 are waste that has to be ground before further processing, like bones and biodegradable eating utensils, they are fed into the mixing room 13 through the first feeding port 11. If the to-be-processed objects 1 are simple food waste that does not need to be ground, they can be fed into the mixing room 13 through the second feeding port 12. Specifically, the output 14 may be equipped with an electronic valve. The electronic valve is connected to the control device 30, so that a user can control the output flow of the processed mixture of the to-be-processed objects 1 coming out through the electronic valve by operating the control device 30 for convenient recycling or other purposes.

In a preferred embodiment of the present invention, the first feeding port 11 and the second feeding port 12 are located at the same side of the processing barrel 10. Most preferably, the first feeding port 11 and the second feeding port 12 are located at the upper side of the processing barrel 10, without limitation, so that a user can introduce the to-be-processed objects 1 easily and effortlessly. In practical use, a user may build a platform with stairs beside the organic-waste-recycling apparatus 100 for the user to stand and feed the to-be-processed objects 1. This frees the user from the inconvenience of moving between the first feeding port 11 and the second feeding port 12. In another preferred embodiment of the present invention, the output 14 is located on the processing barrel 10 and at the side opposite to the side where the first feeding port 11 and the second feeding port 12 are located.

Figure 2:
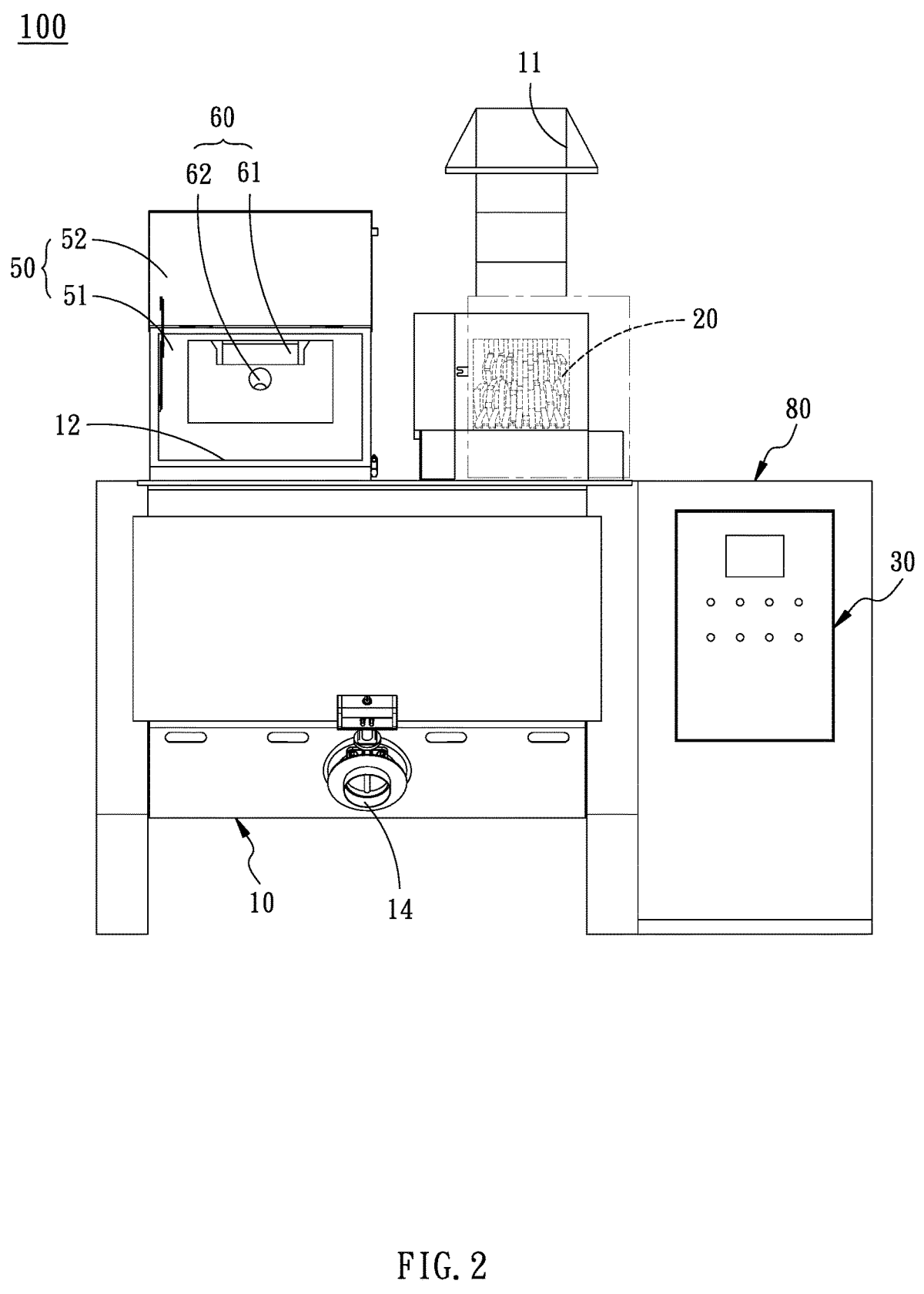

Referring to FIG. 2, the grinding device 20 is arranged between the first feeding port 11 and the mixing room 13. Specifically, the grinding device 20 is installed in the processing barrel 10. The to-be-processed objects 1 fed through the first feeding port 11 are ground by the grinding device 20 before entering the mixing room 13 as scraps for easy recycling. The grinding device 20 may grind the to-be-processed objects 1 using, for example, a plurality of knives, without limitation.

The control device 30 has a temperature-controlling unit 31 and a humidity-controlling unit 32. The control device 30 is electrically connected to the temperature-controlling unit 31 and the humidity-controlling unit 32. The temperature-controlling unit 31 may be installed at the bottom of the processing barrel 10, and the humidity-controlling unit 32 may be installed at the top of the mixing room 13. However, the temperature-controlling unit 31 and the humidity-controlling unit 32 may be located elsewhere, without limitation. The temperature-controlling unit 31 adjusts the fermentation temperature in the mixing room 13 by means of a heat source, and the humidity-controlling unit 32 adjusts the fermentation humidity in the mixing room 13 by means of a mist maker. By using the temperature-controlling unit 31 and the humidity-controlling unit 32 to adjust the temperature and the humidity in the mixing room 13, the disclosed apparatus 100 provides the to-be-processed objects 1 with an environment that facilitates fermentation, thereby ensuring effective and efficient fermentation of the to-be-processed objects 1 while shortening the fermentation cycle of the to-be-processed objects 1. The fermented to-be-processed objects 1 may be used as feeds for economic animals, such as hogs, and chickens, or may be used as compost, without limitation.

Specifically, the temperature-controlling unit 31 heats the processing barrel 10 to elevate the temperature in the processing barrel 10. The processing barrel 10 then transfers the heat into the mixing room 13. The to-be-processed objects 1 fed into the mixing room 13 are aggregated at the bottom of the mixing room 13 by gravity. As such, the temperature-controlling unit 31 located at the bottom of the processing barrel 10 is better located to effectively and efficiently heat and ferment the to-be-processed objects 1 than if it were located elsewhere because the heat transfer distance is minimized.

In a preferred embodiment of the present invention, the fermentation temperature ranges between 50° C. and 80° C. Specifically, if the fermentation temperature is below 50° C., the environment in the mixing room 13 would be too cold to allow the to-be-processed objects 1 to be well heated and fermented. If the fermentation temperature is higher than 80° C., the environment in the mixing room 13 would be so hot that the moisture in the to-be-processed objects 1 vaporizes undesirably fast and effective fermentation is prevented. In a most preferred embodiment of the present invention, the fermentation temperature may be 50, 55, 60, 65, 70, 75 or 80° C. The temperature-controlling unit 31 is designed to reliably hold the fermentation temperature in the mixing room 13 within the above-indicated temperature range.

In a preferred embodiment of the present invention, the fermentation humidity ranges between 50% and 70%. Specifically, if the fermentation humidity is lower than 50% or higher than 70%, the to-be-processed objects 1 are prevented from effective fermentation. In a most preferred embodiment of the present invention, the fermentation humidity may be 50%, 55%, 60%, 65% or 70%. The humidity-controlling unit 32 is designed to reliably hold the fermentation humidity in the mixing room 13 within the above-indicated humidity range.

Figure 3:
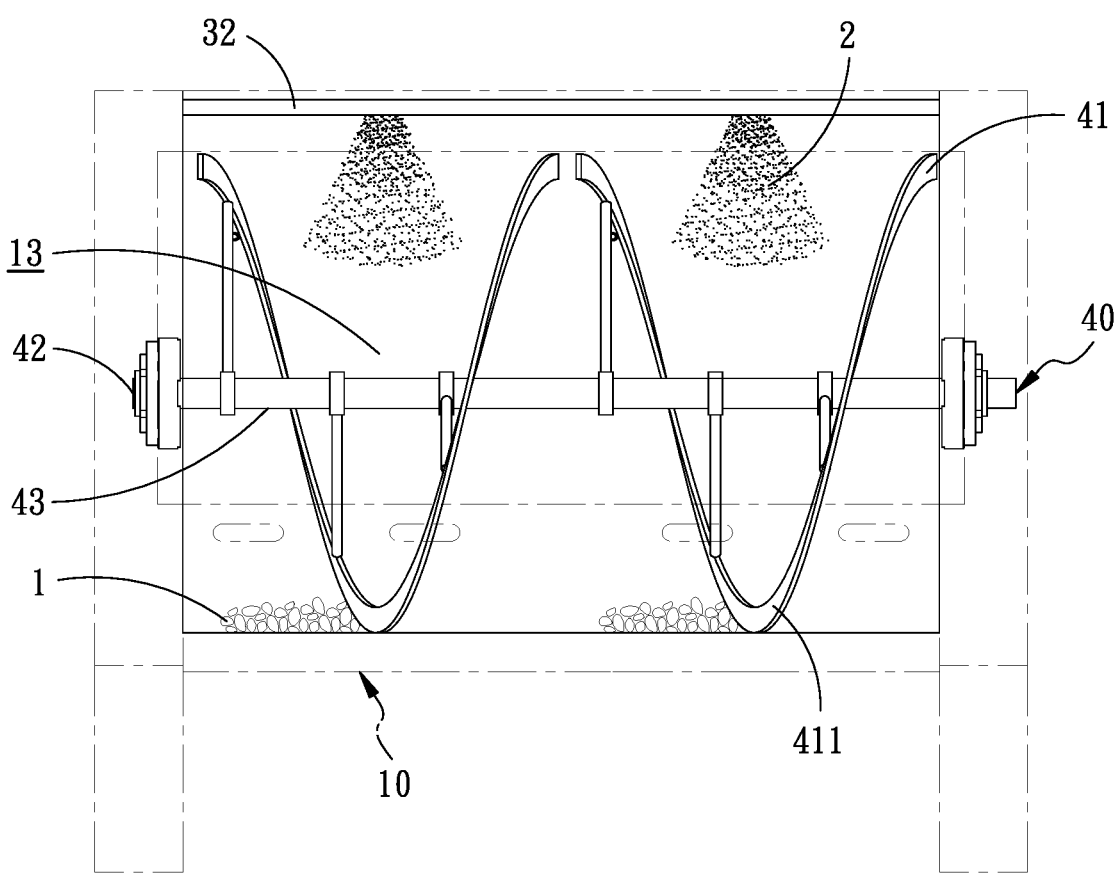
FIG. 3 and FIG. 4 are applied views of a processing barrel of the organic-waste-recycling apparatus.
Figure 4:
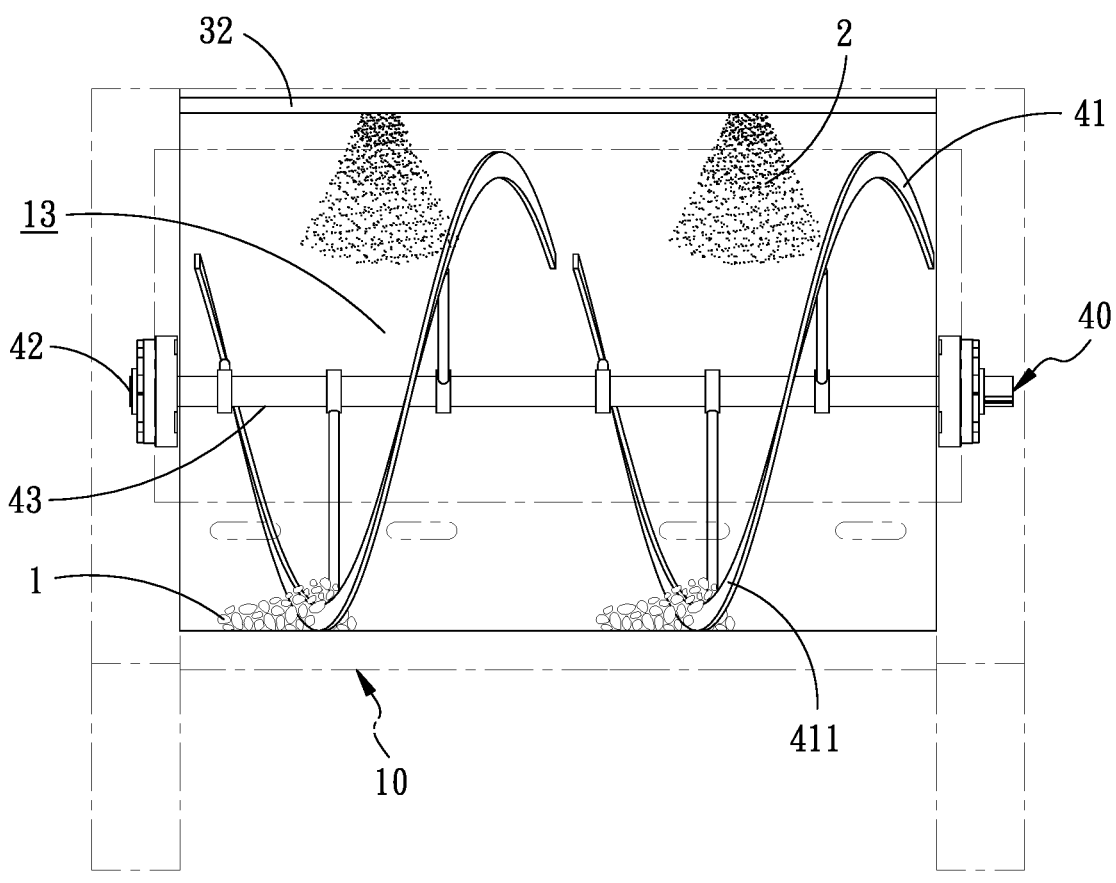

Referring to FIG. 3 and FIG. 4, the stirring device 40 is installed in the mixing room 13. The stirring device 40 has at least one helical cutter 41. The stirring device 40 is connected to a power source 42. The power source 42 serves to rotate the helical cutter 41 in the mixing room 13. Specifically, the helical cutter 41 rolls and blends the to-be-processed objects 1 fed into the mixing room 13 through the first feeding port 11 or the second feeding port 12, so as to ensure that the to-be-processed objects 1 are heated evenly as they are rolling in the mixing room 13. This is helpful for prevention of uneven heating that might otherwise happen when some to-be-processed objects 1 first fed into the processing barrel 10 stay at the bottom of the processing barrel 10 and get heated more than other to-be-processed objects 1 that are subsequently fed into the processing barrel 10 and separated from the heat source by the first fed to-be-processed objects 1.

In a preferred embodiment of the present invention, the power source 42 is electrically connected to the control device 30, so that a user is allowed to adjust the rotation speed of the helical cutter 41 or the control device 30 can automatically adjust the rotation speed of the helical cutter 41.

In a preferred embodiment of the present invention, the helical cutter 41 has a shoveling portion 411 formed at the middle section of the helical cutter 41. As the helical cutters 41 roll in the mixing room 13, the to-be-processed objects 1 come into contact with the helical cutter 41 and thus tumble over the shoveling portion 411 to the opposite side of the helical cutter 41. In this way, the to-be-processed objects 1 are made to continuously roll in the mixing room 13 as they get heated evenly, thereby improving effectiveness of heating for the to-be-processed objects 1. In another preferred embodiment of the present invention, there are two such helical cutters 41. In still another preferred embodiment of the present invention, the stirring device 40 has a rotatory shaft 43, and the helical cutter 41 is mounted around and driven to rotate by the rotatory shaft 43, so that the tumbling to-be-processed objects 1 move through the gap between the rotatory shaft 43 and the shoveling portion 411, thereby ensuring even heating for the to-be-processed objects 1 and helping the to-be-processed objects 1 to gradually cake as they undergo fermentation.

The guiding device 50 is mounted on the processing barrel 10. The guiding device 50 is located over the second feeding port 12. The guiding device 50 serves to guide a water vapor 2 generated in the mixing room 13 back to the mixing room 13. Specifically, the water vapor 2 is generated as a result of that the humidity-controlling unit 32 adjusts the humidity in the mixing room 13. The water vapor 2 condenses on the guiding device 50 as condensate and then flows downward back to the mixing room 13 along the surface of the guiding device 50. This reduces evaporation of the water vapor 2 from the mixing room 13.

In a preferred embodiment of the present invention, the guiding device 50 has an inclined guiding plate 51 and an inclined covering plate 52. The inclined covering plate 52 is pivotable with respect to the second feeding port 12 between an open position and a closed position. When the inclined covering plate 52 is at the closed position, it forms an included angle with the inclined guiding plate 51, so that condensate of the water vapor 2 formed on the guiding device 50 flows back to the mixing room 13 along the inclined surfaces of the inclined guiding plate 51 and the inclined covering plate 52. The inclined covering plate 52 also works as a cover of the second feeding port 12 for a user to operate to open or close the second feeding port 12.

In a preferred embodiment of the present invention, the disclosed apparatus is further provided with a monitoring device 60. The monitoring device 60 has a lighting unit 61 and an image-capturing unit 62. The monitoring device 60 is electrically connected to the control device 30. The lighting unit 61 and the image-capturing unit 62 are mounted on the inclined guiding plate 51. Specifically, the lighting unit 61 illumines the mixing room 13 so that the image-capturing unit 62 can capture clear images of the to-be-processed objects 1 in the mixing room 13 during fermentation for a user to monitor fermentation of the to-be-processed objects 1. In a most preferred embodiment of the present invention, the image-capturing unit 62 may be wirelessly connected to a mobile device, such as a smartphone, or a tablet. The image-capturing unit 62 sends the images inside the mixing room 13 in a real-time manner, so that a user can check how the to-be-processed objects 1 are fermented.

Figure 5:
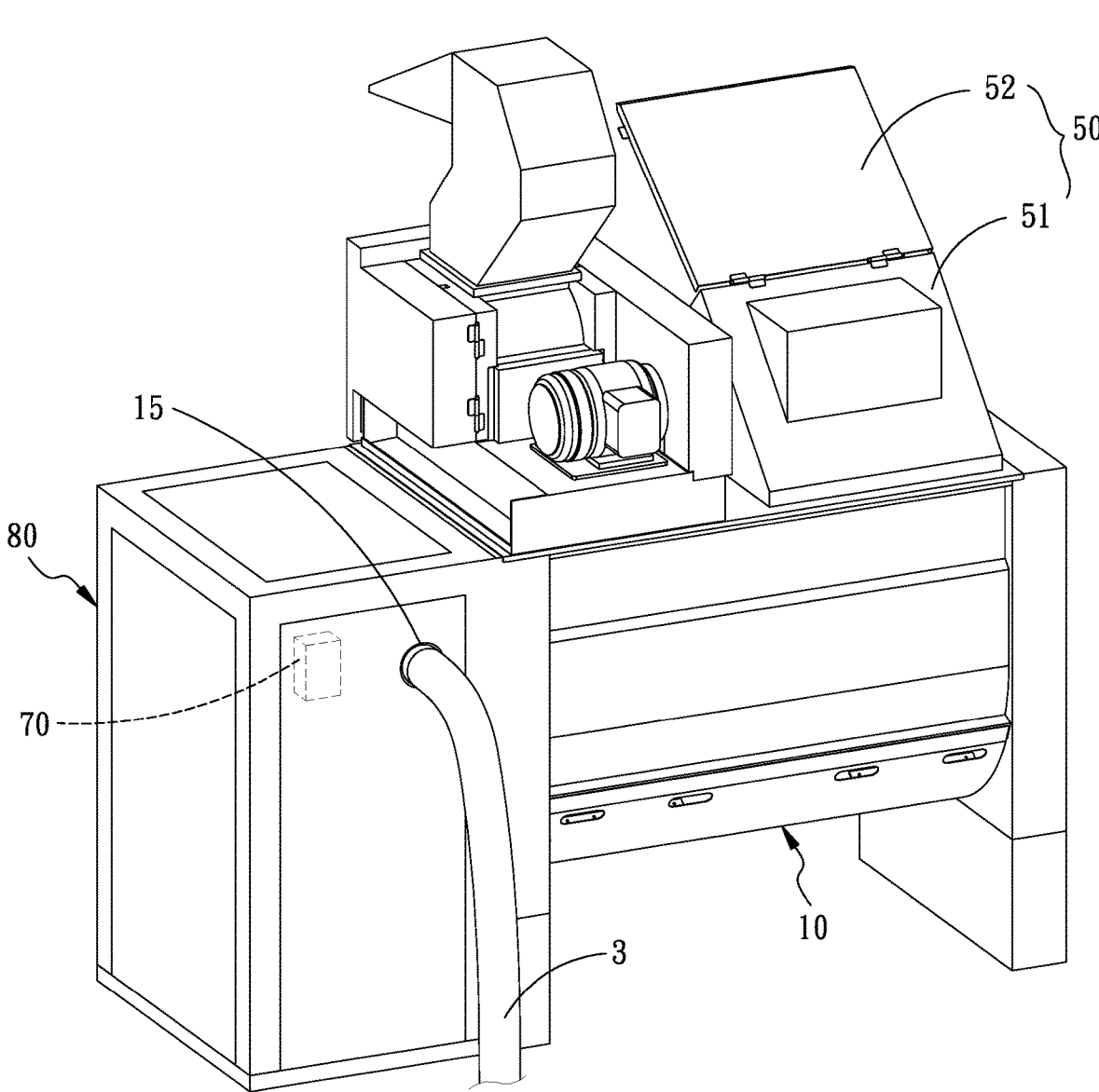
FIG. 5 is a schematic perspective view of an organic-waste-recycling according to another apparatus preferred embodiment of the present invention.

Referring to FIG. 5, in a preferred embodiment of the present invention, the processing barrel 10 has a vent 15. The vent 15 is communicated with the mixing room 13. The vent 15 is open to the ambient air outside the processing barrel 10 through a venting channel 3 so that odor in the mixing room 13 can be exhausted and fresh air can be introduced. The vent 15 may be located at the back side of the processing barrel 10, without limitation. In a most preferred embodiment of the present invention, the disclosed apparatus 100 is further provided with a filtering device 70. The filtering device 70 is arranged between the vent 15 and the mixing room 13 for blocking odor from escaping from the mixing room 13 more effectively. The filtering device 70 may have a filter made of a material that contains active carbon or may have a biological filter, without limitation.

In a preferred embodiment of the present invention, the disclosed apparatus 100 is further provided with a housing 80. The processing barrel 10 is located at one side of and inside the housing 80, while the control device 30 is located at an opposite side of and inside the housing 80.

To sum up, the present invention has the following features:

1. With the grinding device 20, the disclosed apparatus 100 can grind large pieces of to-be-processed objects 1 into scraps, thereby facilitating subsequent processing of the to-be-processed objects 1 for recycling.
2. With the helical cutter 41 rolling and blending the to-be-processed objects 1 in the mixing room 13, the disclosed apparatus 100 can evenly heat the to-be-processed objects 1 as they roll in the mixing room 13, so as to ensure effective and efficient fermentation and further use of the to-be-processed objects 1.
3. With the temperature-controlling unit 31 and the humidity-controlling unit 32 that adjust the fermentation temperature and the fermentation humidity in the mixing room 13, the disclosed apparatus 100 can provide the to-be-processed objects 1 with an environment that is favorable to fermentation, so the to-be-processed objects 1 need not to be retained in the apparatus for a prolonged period, thereby ensuring effective and efficient fermentation of the to-be-processed objects 1.
4. With the guiding device 50 that guides the water vapor 2 back to the mixing room 13, the disclosed apparatus 100 can prevent water vapor 2 from escaping from the mixing room 13.

The effects recited previously do not exclude the existence of other effects. All effects that can be derived by people skilled in the art by referring to the description, the claims, and/or the drawing are also considered as effects of the present invention. Hence, effects of the present invention are not limited to what has been described.

The preferred embodiments described previously are merely illustrative and not intended to limit the scope of the present invention. All equivalent changes or modifications made thereto which do not depart from the concept of the present invention should be encompassed by the appended claims.

What is claimed is:

1. An organic-waste-recycling apparatus for fast formation of compost, configured to process to-be-processed objects for recycling, the organic-waste-recycling apparatus comprising:

a processing barrel, having a first feeding port, a second feeding port, a mixing room, and an output, wherein the first feeding port, the second feeding port, and the output are communicated with the mixing room, and the to-be-processed objects are fed into the mixing room through the first feeding port or the second feeding port;

a grinding device, arranged between the first feeding port and the mixing room, the grinding device configured to grind the to-be-processed objects using a plurality of knives;

a control device, having a temperature-controlling unit and a humidity-controlling unit both electrically connected to the control device, wherein the temperature-controlling unit adjusts a fermentation temperature in the mixing room using a heat source, and the humidity-controlling unit adjusts a fermentation humidity in the mixing room using a mist maker;

a stirring device, installed in the mixing room and provided with a helical cutter, the stirring device having a rotatory shaft, the helical cutter is affixed around and driven to rotate by the rotatory shaft, and the helical cutter having a shoveling portion formed at the middle section of the helical cutter, wherein the helical cutter rolls and blends the to-be-processed objects fed through the first feeding port or the second feeding port in the mixing room, so that the to-be-processed objects tumble over the shoveling portion to the opposite side of the helical cutter and are evenly heated while rolling in the mixing room; and a guiding device, mounted on the processing barrel, the guiding device having an inclined guiding plate and an inclined covering plate, wherein the inclined guiding plate is connected to and forms an included angle with the inclined covering plate, and is configured such that the inclined guiding plate and the inclined covering plate guide a water vapor generated in the mixing room back to the mixing room.

2. The organic-waste-recycling apparatus of claim 1, further comprising a housing, wherein the processing barrel is located within one side of the housing and the control device is located within an opposite side of the housing.

3. The organic-waste-recycling apparatus of claim 2, wherein the processing barrel has a vent that is communicated with the mixing room.

4. The organic-waste-recycling apparatus of claim 3, further comprising a filtering device that is arranged between the vent and the mixing room.

5. The organic-waste-recycling apparatus of claim 2, wherein the first feeding port and the second feeding port are located at a same side of the processing barrel.

6. The organic-waste-recycling apparatus of claim 5, wherein the output is located at a side of the processing barrel that is opposite to the side where the first feeding port and the second feeding port are located.

7. The organic-waste-recycling apparatus of claim 1, wherein the helical cutter comprises two helical cutting elements.

8. The organic-waste-recycling apparatus of claim 1, wherein, the fermentation temperature ranges between 50° C. and 80° C.

9. The organic-waste-recycling apparatus of claim 1, wherein the fermentation humidity ranges between 50% and 70%.

10. The organic-waste-recycling apparatus of claim 1, wherein the temperature-controlling unit is installed at a bottom of the processing barrel.

11. The organic-waste-recycling apparatus of claim 1, further comprising a monitoring device having a lighting unit and an image-capturing unit both mounted on the inclined guiding plate.

* * * * *